United States Patent [19]

Cotteret

[11] Patent Number: 5,391,206
[45] Date of Patent: Feb. 21, 1995

[54] METHOD FOR DYEING KERATINOUS FIBERS USING 4-HYDROXYINDOLE AT ACID PH AND COMPOSITION USED

[75] Inventor: Jean Cotteret, Verneuil-sur-Seine, France

[73] Assignee: L'Oreal, Paris, France

[21] Appl. No.: 49,657

[22] Filed: Apr. 12, 1993

Related U.S. Application Data

[63] Continuation of Ser. No. 726,262, Jul. 5, 1991, abandoned.

[30] Foreign Application Priority Data

Jul. 5, 1990 [FR] France ................. 90 08569

[51] Int. Cl.$^6$ ................................ A61K 7/13
[52] U.S. Cl. ........................... 8/408; 8/405; 8/406; 8/407; 8/409; 8/410; 8/411; 8/412; 8/423
[58] Field of Search .............. 8/405, 406, 407, 408, 8/414, 416, 409, 410, 411, 412, 423; 424/70

[56] References Cited

U.S. PATENT DOCUMENTS 5,034,015  7/1991  Juniro et al. ................. 8/405

FOREIGN PATENT DOCUMENTS

| | | |
|---|---|---|
| 2636235 | 3/1990 | France . |
| 3031709 | 4/1982 | Germany . |
| 3441148 | 5/1986 | Germany . |
| 3743769 | 7/1989 | Germany . |
| 2197885 | 6/1988 | United Kingdom . |
| 2211517 | 7/1989 | United Kingdom . |

*Primary Examiner*—Christine Skane
*Assistant Examiner*—Caroline L. Dusheck
*Attorney, Agent, or Firm*—Jacobson, Price, Holman & Stern

[57] ABSTRACT

Method for dyeing keratinous fibres, in particular human keratinous fibres such as hair, characterized in that a composition containing, in a medium appropriate for dyeing:

- at least the coupler 4-hydroxyindole, as well as the salts of this compound;
- at least one oxidation dye precursor; and
- at least one oxidising agent; is applied to said fibres, the pH of the composition applied to the fibres being less than 7.

29 Claims, No Drawings

METHOD FOR DYEING KERATINOUS FIBERS USING 4-HYDROXYINDOLE AT ACID PH AND COMPOSITION USED

This application is a continuation of application Ser. No. 07/726,262, filed Jul. 5, 1991, now abandoned.

The present invention relates to a new method for dyeing keratinous fibres, in particular human keratinous fibres, using 4-hydroxyindole in combination with oxidation bases and an oxidising agent, in an acid medium, and to the compositions used in the course of this method.

It is known to dye keratinous fibres, and in particular human hair, using tinctorial compositions containing, in an alkaline medium, oxidation dye precursors, and in particular p-phenylenediamines or ortho- or para-aminophenols, generally termed "oxidation bases".

It is also known that the shades obtained with these oxidation bases can be varied by combining said bases with couplers, also termed colour modifiers, chosen, in particular, from aromatic meta-diamines, meta-aminophenols and meta-diphenols.

The use of couplers for blues in oxidation dyeing is particularly advantageous for the production of natural or ash shades.

Within the customary framework of oxidation dyeing in an alkaline medium, the use of meta-phenylenediamine derivatives or indole compounds such as 4-hydroxyindole as couplers for blues, in the presence of oxidation bases such as para-phenylenediamine, has already been proposed.

The Applicant has just discovered, surprisingly, that the use of 4-hydroxyindole, as coupler, in combination with oxidation bases in a mixture, prepared for use, with an oxidising agent, at an acid pH, enabled natural and ash dyeings having an improved tinctorial power and a remarkable stability to shampooing, perspiration, chemical treatments and atmospheric agents, such as light, to be obtained.

The present invention therefore relates to a method for dyeing keratinous fibres, in particular human keratinous fibres such as hair, comprising the application to these fibres of at least one composition containing 4-hydroxyindole as coupler, at least one oxidation dye precursor and an oxidising agent, at acid pH.

The invention also relates to a two-component dyeing agent, one component of which comprises 4-hydroxyindole and at least one oxidation dye precursor and the other the oxidising agent at an acid pH, in amounts such that the mixture has an acid pH.

The invention also relates to the ready-to-use composition containing the various agents used for dyeing hair in an acid medium.

Further subjects of the invention will become apparent on reading the description and the examples which follow.

The method for dyeing keratinous fibres and in particular human keratinous fibres such as hair, according to the invention, is essentially characterised in that a composition containing, in a medium appropriate for dyeing:

at least 4-hydroxyindole as coupler, as well as the salts of this compound;
at least one oxidation dye precursor; and
at least one oxidising agent; is applied to said fibres, the pH of the composition applied to the fibres being less than 7.

The oxidation dye precursors or oxidation bases are known compounds which are not themselves dyes and which form a dye by means of an oxidative condensation process, either on themselves or in the presence of a coupler or modifier. These compounds generally comprise an aromatic ring carrying functional groups consisting: either of two amino groups; or of an amino group and a hydroxyl group; these groups being in the para- or ortho-position relative to one another.

The oxidation dye precursors of the para type, used according to the invention, are chosen more particularly from para-phenylenediamines, paraaminophenols and para heterocyclic precursors, such as 2,5-diaminopyridine, 2-hydroxy-5-aminopyridine and 2,4,5,6-tetraaminopyrimidine.

Para-phenylenediamines which may be mentioned are the compounds corresponding to the formula (I):

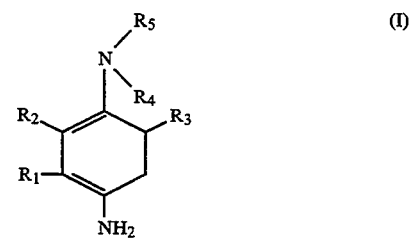

in which $R_1$, $R_2$ and $R_3$, which may be identical or different, represent a hydrogen or halogen atom, an alkyl radical having from 1 to 4 carbon atoms or an alkoxy radical having from 1 to 4 carbon atoms; and $R_4$ and $R_5$, which may be identical or different, represent a hydrogen atom or an alkyl, hydroxyalkyl, alkoxyalkyl, carbamylalkyl, mesylaminoalkyl, acetylaminoalkyl, ureidoalkyl, carbalkoxyaminoalkyl, piperidinoalkyl, or morpholinoalkyl radical; these alkyl or alkoxy groups having from 1 to 4 carbon atoms, or $R_4$ and $R_5$ form, together with the nitrogen atom to which they are bonded, a piperidino or morpholino heterocycle, on condition that $R_1$ or $R_3$ represents a hydrogen atom when $R_4$ and $R_5$ do not represent a hydrogen atom, and the salts of these compounds.

Particularly preferred compounds corresponding to the formula (I) which may be mentioned are p-phenylenediamine, 2-methyl-p-phenylenediamine, 2,6-dimethyl-para-phenylenediamine, 2,5-dimethyl-para-phenylenediamine, 2,3-dimethyl-para-phenylenediamine, methoxy-para-phenylenediamine, chloro-para-phenylenediamine, 2-methyl-5-methoxy-para-phenylenediamine, 2,6-dimethyl-5-methoxy-para-phenylenediamine, N,N-dimethyl-para-phenylenediamine, 3-methyl-4-amino-N,N-diethylaniline, N,N-di-(β-hydroxyethyl)paraphenylenediamine, 3-methyl-4-amino-N,N-di-(β-hydroxyethyl)aniline, 3-chloro-4-amino-N,N-di-(β-hydroxyethyl)aniline, 4-amino-N,N-(ethyl, carbamylmethyl)aniline, 3-methyl-4-amino-N,N-(ethyl, carbamylmethyl)aniline, 4-amino-N,N-(ethyl, β-piperidinoethyl)aniline, 3-methyl-4-amino-N,N-(ethyl, β-piperidinoethyl)aniline, 4-amino-N,N-(ethyl, β-morpholinoethyl)aniline, 3-methyl-4-amino-N,N-(ethyl, β-morpholinoethyl)aniline, 4-amino-N,N-(ethyl, β-acetylaminoethyl)aniline, 4-amino-N-(β-methoxyethyl)aniline, 3-methyl-4-amino-N,N-(ethyl, β-acetylaminoethyl)aniline, 4-amino-N,N-(ethyl, β-mesylaminoethyl)aniline, 3-methyl-4-amino-N,N-(ethyl, β-mesylaminoethyl)aniline, 4-amino-N,N-(ethyl, β-sulphoethyl)aniline, 3-methyl-4-amino-N,N-(ethyl, β-sulphoethyl)aniline, N-[(4'-amino)phenyl]morpholine and N-[(4'-amino)phenyl]piperidine.

These oxidation dye precursors of the para type may be introduced into the tinctorial composition either in the form of the free base or in the form of salts, such as in the form of the hydrochloride, hydrobromide or sulphate.

p-Aminophenols which may be mentioned are p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2-hydroxymethyl-4-aminophenol, 2-(β-hydroxyethyl)-4-aminophenol, 2-methoxy-4-aminophenol, 3-methoxy-4-aminophenol, 2,5-dimethyl-4-aminophenol and 2-methoxymethyl-4-aminophenol.

The oxidation dye precursors of the ortho type are chosen from ortho-aminophenols, such as 1-amino-2-hydroxybenzene, 6-methyl-1-hydroxy-2-aminobenzene and 4-methyl-1-amino-2-hydroxybenzene, and ortho-phenylenediamines.

The oxidation dye precursors used very particularly in accordance with the present invention are:
para-phenylenediamine
2-methyl-para-phenylenediamine
2,6-dimethyl-para-phenylenediamine
para-aminophenol
chloro-para-phenylenediamine.

The oxidising agent is preferably chosen from hydrogen peroxide, urea peroxide, alkali metal bromates and persalts such as perborates and persulphates. Hydrogen peroxide is particularly preferred.

The tinctorial compositions do not contain iodide ions in amounts sufficient to oxidise 4-hydroxyindole and the oxidation dye precursor.

The pH of the composition applied to the keratinous fibres, in particular the hair, has a value of below 7 and is preferably between 3 and 6.9. This pH is adjusted using acidifying agents well known in the field of dyeing of keratinous fibres, and in particular of human hair, such as inorganic acids, such as hydrochloric acid or phosphoric acid, or organic acids, such as carboxylic acids, such as tartric acid or citric acid.

4-Hydroxyindole is present in the composition applied to the keratinous fibres in proportions of preferably between 0.01 and 3.5% by weight relative to the total weight of the composition.

The compositions, defined above, applied in the dyeing of keratinous fibres may also contain, in addition to 4-hydroxyindole, other couplers known per se, such as meta-diphenols, meta-aminophenols, meta-phenylenediamines, meta-N-acylaminophenols, meta-ureidophenols, meta-carbalkoxyaminophenols, α-naphthol and couplers containing an active methylene group, such as the diketone compounds and pyrazolones.

Amongst these couplers which may be used in addition to the 4-hydroxyindole, the following may be mentioned: 2,4-dihydroxyphenoxyethanol, 2,4-dihydroxyanisole, meta-aminophenol, resorcinol, resorcinol monomethyl ether, 2-methylresorcinol, pyrocatechol, 2-methyl-5-N-(β-hydroxyethyl)aminophenol, 2-methyl-5-N-(β-mesylaminoethyl)aminophenol, 6-hydroxybenzomorpholine, 2,4-diaminoanisole, 2,4-diaminophenoxyethanol, 6-aminobenzomorpholine, [2-N-(β-hydroxyethyl)amino-4-amino]-phenoxyethanol, 2-amino-4-N-(β-hydroxyethyl)aminoanisole, (2,4-diamino)phenyl-β,γ-dihydroxypropyl ether, 2,4-diaminophenoxyethylamine, 1,3-dimethoxy-2,4-diaminobenzene, 2-methyl-5-aminophenol, 2,6-dimethyl-3-aminophenol, 3,4-methylenedioxyphenol and 3,4-methylenedioxyaniline and their salts.

The compositions defined above may also contain direct dyes such as nitro derivatives of the benzene series, azo dyes, anthraquinone dyes, triphenylmethanes, or xanthene or azine dyes well known to those skilled in the art. They may also contain rapid oxidation dyes.

These compositions may also contain anionic, cationic, nonionic or amphoteric surface-active agents or their mixtures.

Amongst these surface-active agents, the following may be mentioned: fatty alcohol alkylbenzenesulphonates, alkylnaphthalenesulphonates, sulphates, ether-sulphates and sulphonates, quaternary ammonium salts, such as trimethylcetylammonium bromide, cetylpyridiniumbromide, optionally oxyethylenated fatty acid ethanolamides, polyoxyethylenated acids, alcohols or amines, polyglycerolated alcohols, polyoxyethylenated or polyglycerolated alkylphenols and polyoxyethylenated alkyl sulphates.

The tinctorial compositions are generally aqueous but they may also contain organic solvents in order to dissolve compounds which would not be sufficiently soluble in water. Among these solvents, the following may be mentioned as examples: $C_2-C_4$ lower alkanols, such as ethanol and isopropanol, glycerol, glycols or glycol ethers, such as 2-butoxyethanol, ethylene glycol, propylene glycol, diethylene glycol monoethyl ether and monomethyl ether, and propylene glycol monoethyl ether and monomethyl ether, and also aromatic alcohols, such as benzyl alcohol or phenoxyethanol, or mixtures of these solvents.

The composition applied to the hair may also contain thickeners chosen in particular from sodium alginate, gum arabic, cellulose derivatives, such as methyl cellulose, hydroxyethyl cellulose, hydroxypropyl cellulose, hydroxymethyl cellulose and carboxymethyl cellulose, optionally crosslinked acrylic acid polymers and xanthan gum. It is also possible to use inorganic thickeners such as bentonite.

The composition may also contain antioxidants, chosen in particular from sodium sulphite, thioglycolic acid, sodium bisulphite, ascorbic acid and hydroquinone, as well as other cosmetically acceptable adjuvants when the composition is intended to be used for dyeing human keratinous fibres, such as penetration agents, sequestering agents, preservatives, buffers, perfumes, and the like.

The composition applied to the hair may be in diverse forms, such as liquids, creams or gels or in any other form appropriate for carrying out hair dyeing. It may be packaged in an aerosol can in the presence of a propellant.

The invention also relates to the ready-to-use composition used in the method defined above.

According to a preferred embodiment, the method comprises a preliminary step consisting in storing separately on the one hand the composition containing, in a medium appropriate for dyeing, the 4-hydroxyindole coupler and the oxidation dye precursors, in the form of a component (A), and, on the other hand, a composition containing the oxidising agent as defined above, in the form of a component (B), and in preparing a mixture thereof for use before applying this mixture to the keratinous fibres, as indicated above.

The composition applied to the keratinous fibres results from a mixture of 10 to 90% of the component (A) with 90 to 10% of the component (B) containing an oxidising agent.

The invention also relates to an agent for dyeing keratinous fibres, in particular hair, essentially characterised in that it comprises at least two components, one of the components consisting of the component (A) defined above and the other consisting of the component (B), also defined above, the pH of the components (A) and (B) being such that, after mixing in proportions of 90 to 10% in respect of component (A) and of 10 to 90% in respect of component (B), the resulting composition has a pH of less than 7.

In this embodiment the component (A), which contains at least 4-hydroxyindole and an oxidation dye precursor, may have a pH of between 3 and 10.5 and may be adjusted to the chosen value using alkalinising agents customarily used in dyeing keratinous fibres, such as ammonia, alkali metal carbonates or alkanolamines, such as mono-, di- and triethanolamines and their derivatives, or conventional acidifying agents, such as inorganic acids, such as hydrochloric or phosphoric acid, or organic acids, such as carboxylic acids, such as tartaric or citric acid.

This composition does not contain iodide ions in amounts sufficient to oxidise 4-hydroxyindole and the oxidation dye precursor.

This composition may contain the various other adjuvants mentioned above, in particular couplers other than 4-hydroxyindole.

The system comprising oxidation dye precursors of the para and/or ortho type and also the couplers are present in proportions of preferably between 0.05 and 7% by weight relative to the total weight of the component (A). The concentration of 4-hydroxyindole may vary between 0.01 and 4% by weight relative to the total weight of the component (A).

The surface-active agents are present in the component (A) in proportions of 0.1 to 55% by weight. If the mixture contains solvents in addition to water, the latter are present in proportions of between 0.5 and 40% by weight, and in particular of between 5 and 30% by weight, relative to the total weight of the component (A). The thickeners are preferably present in proportions of between 0.1 and 5%, and in particular of between 0.2 and 3%, by weight. The antioxidants mentioned above are preferably present in the component (A) in proportions of between 0.02 and 1.5% by weight relative to the total weight of the component (A).

The component (B) containing the oxidising agent as defined above has a pH of less than 7. This pH may have a minimum value of 1 and preferably less than 5. This component (B) may be acidified using the same type of acidifying agents as those used for the component (A).

It may be in the form of a liquid thickened to a greater or lesser extent or of a milk or gel.

This two-component dyeing agent may be packaged in a multi-compartment device or dyeing kit, or any other multi-compartment packaging system in which one compartment contains the component (A) and the second contains the component (B); these devices may be fitted with means permitting the desired mixture to be delivered onto the hair, such as the devices described in the Applicant's Patent U.S. Pat. No. 4,823,985.

The invention also relates to the use of 4-hydroxyindole as a coupler for dyeing keratinous fibres in an acid medium, in combination with oxidation dye precursors.

According to the invention, the dyeing method consists in applying the mixture obtained to the hair, leaving it on the hair for 3 to 40 minutes, then rinsing the hair and optionally shampooing.

It is also possible, according to the invention, separately to apply a composition containing the 4-hydroxyindole coupler, the oxidation dye precursor and the oxidising agent in such a way that the mixture forming in situ on the fibres has a pH of less than 7, as defined above.

The following examples are intended to illustrate the invention without, however, having a limiting character.

EXAMPLES 1 TO 6

Hair is dyed by applying a mixture, prepared for use, of the dyeing composition (A) and the oxidising composition (B) to grey hair which is 90% white.

This mixture has the pH indicated in the table of examples which follow. This mixture is allowed to act for 30 minutes and the hair is then rinsed and shampooed. After drying, the hair is dyed in the shade specified at the bottom of the table below.

| | in g | | |
|---|---|---|---|
| | 1 | 2 | 3 |
| A) Dyeing composition | | | |
| 4-hydroxyindole | 0.399 | 0.133 | 0.266 |
| 2,6-dimethyl-para-phenylenediamine.2HCl | 0.627 | | |
| 2,3-dimethyl-para-phenylenediamine.2HCl | | | 0.418 |
| 2-methyl-para-phenylenediamine.2HCl | | 0.366 | |
| Meta-aminophenol | | 0.109 | |
| α-naphthol | | 0.144 | |
| Monoethanolamine qs pH | 8.9 | 9.0 | 9.0 |
| Carrier 2 | X | X | X |
| Water qs | 100 | 100 | 100 |
| B) Oxidising composition | | | |
| 20 volume hydrogen peroxide solution | | | |
| Phosphoric acid qs pH | 1.2 | 1.2 | 1.2 |
| pH of wt/wt A + B mixture | 6.3 | 6.5 | 6.5 |
| Shades obtained: | violet | pearly ash violet | light ash blue |

| | 4 | 5 | 6 |
|---|---|---|---|
| A) Dyeing composition | | | |
| 4-hydroxyindole | 0.266 | 0.399 | 0.399 |
| Para-phenylenediamine | | 0.324 | |
| Para-aminophenol | 0.436 | | 0.327 |
| 2-methyl-5-N-(β-hydroxyethyl)aminophenol | 0.334 | | |
| Monoethanolamine qs pH | 9.9 | 9.8 | 9.8 |
| Carrier 1 | X | | |
| Carrier 3 | | X | X |
| Water qs | 100 | 100 | 100 |
| B) Oxidising composition | | | |
| 20 volume hydrogen peroxide solution | | | |
| Phosphoric acid qs pH | 1.2 | 1.5 | 1.5 |
| pH of wt/wt A + B mixture | | 5.5 | 5.5 |
| pH of ⅓ A + ⅔ B mixture | 5.0 | | |
| Shades obtained: | light ash blond | pearly ash | chestnut |

EXAMPLE 7

| DYEING COMPOSITION | |
|---|---|
| 2,5-diaminonitrobenzene | 0.3 g |
| 4-hydroxyindole | 0.25 g |
| Para-phenylenediamine | 0.4 g |
| Meta-aminophenol | 0.15 g |
| Sodium lauryl ether sulphate containing 2 moles of ethylene oxide, sold as a formulation containing 28% of AS | 4.2 g AS |
| Oxyethylenated nonylphenol containing 9 moles of ethylene oxide | 1.0 g |
| Ethylene glycol monobutyl ether | 9.5 g |
| Sodium metabisulphite containing 35% of AS | 0.45 g AS |
| Monoethanolamine qs pH = 8.4 | |
| Sequestering agent qs | |
| Water qs | 100 g |

Weight for weight mixture with oxidising composition: 20 volume hydrogen peroxide solution—pH: 1.3 using phosphoric acid.

Spontaneous pH of the mixture: 6.3.

Application: as in the preceding Examples 1 to 6.

An iridescent deep auburn chestnut dyeing is obtained on natural grey hair which is 90% white.

| DYEING CARRIER 1 | |
|---|---|
| Nonylphenol containing 4 moles of ethylene oxide, sold under the name SINNOPAL NP4 by HENKEL | 25.5 g |
| Nonylphenol containing 9 moles of ethylene oxide, sold under the name SINNOPAL NP9 by HENKEL | 17.5 g |
| Ethylene glycol monoethyl ether | 7.0 g |
| Propylene glycol | 10.5 g |
| Dipropylene glycol | 0.5 g |
| Ethyl alcohol | 2.0 g |
| Monoethanolamine lauryl ether sulphate, sold under the name SACTIPON 2 OM 29 by LEVER as a formulation containing 28% of AS | 4.2 g AS |
| Sodium alkyl ether sulphate containing 28% of AS | 0.8 g AS |
| Aqueous sodium metabisulphite solution containing 35% of AS | 0.45 g AS |
| Sodium acetate | 0.8 g |
| Antioxidant, sequestering agent qs | |

| DYEING CARRIER 2 | |
|---|---|
| Polyglycerolated oleyl alcohol containing 2 moles of glycerol | 4.0 g |
| Polyglycerolated oleyl alcohol containing 4 moles of glycerol, containing 78% of AS | 5.69 g AS |
| Oleic acid | 3.0 g |
| Oleylamine containing 2 moles of ethylene oxide, sold under the name ETHOMEEN O 12 by AKZO | 7.0 g |
| Diethylaminopropyl laurylaminosuccinamate, sodium salt containing 55% of AS | 3.0 g AS |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Aqueous sodium metabisulphite solution containing 35% of AS | 0.45 g AS |
| Ammonium acetate | 0.8 g |
| Antioxidant, sequestering agent qs | |

| DYEING CARRIER 3 | |
|---|---|
| Nonylphenol containing 4 moles of ethylene oxide, sold under the name SINNOPAL NP4 by HENKEL | 25.5 g |
| Nonylphenol containing 9 moles of ethylene oxide, sold under the name SINNOPAL NP9 by HENKEL | 17.5 g |
| Ethylene glycol butyl ether | 7.0 g |
| Propylene glycol | 11.0 g |
| Ethyl alcohol | 2.0 g |
| Monoethanolamine lauryl ether sulphate, sold under the name SACTIPON 2 OM 29 by LEVER as a formulation containing 28% of AS | 5.0 g AS |
| Aqueous sodium metabisulphite solution containing 35% of AS | 0.45 g AS |
| Sodium acetate | 0.8 g |
| Antioxidant, sequestering agent qs | |

I claim:

1. A method for dyeing keratinous fibre, which comprises applying to the keratinous fibre a composition resulting from a mixture of 90 to 10% of a component (A) with 10 to 90% of a component (B), said component (A) consisting of a composition containing, in a medium appropriate for dyeing, from 0.01 to 4% by weight, relative to the total weight of the component (A), of at least 4-hydroxyindole or a salt thereof as coupler and at least one oxidation dye precursor, the oxidation dye precursors and the couplers being present in proportions from 0.05 to 7% by weight, relative to the total weight of component (A), and said component (B) consisting of a composition containing an oxidizing agent in a sufficient amount to oxidize the coupler and the oxidation dye precursor contained in component (A) and an acid component in a medium appropriate for dyeing, the acid component being present in a sufficient amount such that, after mixing component (A) and component (B) in the above-mentioned proportions, the resulting composition has a pH of less than 7, said resulting composition being substantially free from an amount of iodide ions sufficient to oxidize 4-hydroxyindole and the oxidation dye precursor.

2. A method according to claim 1, wherein the oxidation dye precursor is a member selected from the group consisting of a para-phenylenediamine, a para-aminophenol and a para-heterocyclic precursor.

3. Method according to claim 2, wherein
the para-phenylenediamine is a compound corresponding to the formula:

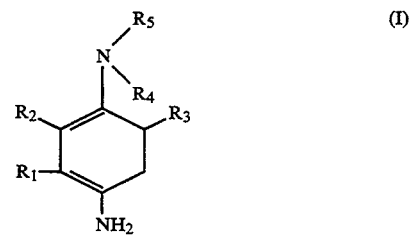

in which $R_1$, $R_2$ and $R_3$, which may be identical or different, represent a hydrogen or halogen atom, an alkyl radical having from 1 to 4 carbon atoms or an alkoxy radical having from 1 to 4 carbon atoms; and $R_4$ and $R_5$, which may be identical or different, represent a hydrogen atom or an alkyl, hydroxyalkyl, alkoxyalkyl, carbamylalkyl, mesylaminoalkyl, acetylaminoalkyl, ureidoalkyl, carbalkoxyaminoalkyl, piperidinoalkyl, or morpholinoalkyl radical; each alkyl or alkoxy groups having from 1 to 4 carbon atoms, or $R_4$ and $R_5$ form, together with the nitrogen atom to which they are bonded, a piperidino or morpholino heterocycle, on condition that $R_1$ or $R_3$ represents a hydrogen atom when $R_4$ and $R_5$ do not represent a hydrogen atom, or a salt thereof.

4. A method according to claim 3, wherein
the compound of formula (I) is p-phenylenediamine, 2-methyl-p-phenylenediamine, methoxy-para-phenylenediamine, chloro-para-phenylenediamine, 2,6-dimethyl-para-phenylenediamine, 2,3-dimethyl-para-phenylenediamine, 2,5-dimethyl-para-phenylenediamine, 2-methyl-5-methoxy-para-phenylenediamine, 2,6-dimethyl-5-methoxy-para-phenylenediamine, N,N-dimethyl-para-phenylenediamine, 3-methyl-4-amino-N,N-diethylaniline, N,N-di-($\beta$-hydroxyethyl)para-phenylenediamine, 3-methyl-4-amino-N,N-di-($\beta$-hydroxyethyl)aniline, 3-chloro-4-amino-N,N-di-($\beta$-hydroxyethyl)aniline, 4-amino-N,N-(ethyl, carbamylmethyl)aniline, 3-methyl-4-amino-N,N-(ethyl, carbamylmethyl)aniline, 4-amino-N,N-(ethyl,$\beta$-piperidinoethyl)aniline, 3-methyl-4-amino-N,N-(ethyl,$\beta$-piperidinoethyl)aniline, 4-amino-N,N-(ethyl,$\beta$-morpholinoethyl)aniline, 3-methyl-4-amino-N,N-(ethyl,$\beta$-morpholinoethyl)aniline, 4-amino-N,N-(ethyl,$\beta$-acetylaminoethyl)aniline, 4-amino-N,($\beta$-methoxyethyl)aniline, 3-methyl-4-amino-N,N-(ethyl,$\beta$-acetylaminoethyl)aniline, 4-amino-N,N-(ethyl,$\beta$-mesylaminoethyl)aniline, 3-methyl-4-amino-N,N-(ethyl,$\beta$-mesylaminoethyl)aniline, 4-amino-N,N-(ethyl,$\beta$-sulphoethyl)aniline, 3-methyl-4-amino-N,N-(ethyl,$\beta$-sulphoethyl)aniline, N-[(4'-amino)-phenyl]morpholine or N-[(4'-amino)phenyl]piperidine, in the form of the free base or a salt thereof.

5. Method according to claim 2, wherein
the p-aminophenol is p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2-hydroxymethyl-4-aminophenol, 2-($\beta$-hydroxyethyl)-4-aminophenol, 2-methoxy-4-aminophenol, 3-methoxy-4-aminophenol, 2,5-dimethyl-4-aminophenol or 2-methoxymethyl-4-aminophenol.

6. A method according to claim 1, wherein the oxidation dye precursor is an oxidation dye precursor selected from the group consisting of an ortho-aminophenol and an ortho-phenylenediamine.

7. A method according to claim 1, wherein the oxidizing agent is a member selected from the group consisting of hydrogen peroxide, urea peroxide, alkali metal bromate and persalt.

8. A method according to claim 1, wherein the pH of the composition applied to the keratinous fibre is between 3 and 6.9.

9. A method according to claim 1, wherein the composition for dyeing keratinous fibre contains, in addition to the 4-hydroxyindole coupler, another coupler selected from the group consisting of a meta-diphenol, a meta-aminophenol, a meta-phenylenediamine, a meta-N-acylaminophenol, a meta-ureidophenol, a meta-carbalkoxyaminophenol, $\alpha$-naphthol and a coupler containing an active methylene group selected from the group consisting of a diketone compound and a pyrazolone.

10. A method according to claim 9, wherein
the coupler is 2,4-dihydroxyphenoxyethanol, 2,4-dihydroxyanisole, meta-aminophenol, resorcinol, resorcinol monomethyl ether, 2-methyl-resorcinol, pyrocatechol, 2-methyl-5-N-($\beta$-hydroxyethyl)aminophenol, 2-methyl-5-N-($\beta$-mesylaminoethyl)aminophenol, 6-hydroxybenzomorpholine, 2,4-diaminoanisole, 2,4-diaminophenoxyethanol, 6-aminobenzomorpholine, [2-N-($\beta$-hydroxyethyl)amino-4-amino]-phenoxyethanol, 2-amino-4-N-($\beta$-hydroxyethyl)aminoanisole, (2,4-diamino)phenyl-$\beta$,$\gamma$-dihydroxypropyl ether, 2,4-diaminophenoxyethylamine, 1,3-dimethoxy-2,4-diaminobenzene, 2-methyl-5-aminophenol, 2,6-dimethyl-3-aminophenol, 3,4-methylenedioxyphenol or 3,4-methylenedioxyaniline or a salt thereof.

11. A method according to claim 1, wherein the composition also contains a direct dye or a rapid oxidation dye.

12. A method according to claim 1, wherein the composition contains anionic, cationic, nonionic or amphoteric surface-active agent or a mixture thereof; thickener, antioxidant or any other cosmetically acceptable adjuvant.

13. A method according to claim 1, in which the medium appropriate for dyeing consists of water and a solvent selected from the group consisting of $C_2$–$C_4$ lower alkanol, glycerol, glycol, glycol ether and aromatic alcohol or a mixture thereof.

14. A dyeing method according to claim 1, wherein the composition is applied to the keratinous fibre and is left on the keratinous fibre for from 3 to 40 minutes, the keratinous fibre is rinsed and shampooing is optionally carried out before rinsing again and drying.

15. The method of claim 1, wherein the acid component is an inorganic acid or an organic acid.

16. The method of claim 15, wherein the inorganic acid is hydrochloric acid or phosphoric acid.

17. The method of claim 15, wherein the organic acid is a carboxylic acid.

18. The method of claim 17, wherein the carboxylic acid is tartaric acid or citric acid.

19. An agent for dyeing keratinous fibre, which comprises at least two components: a component (A) consisting of a composition containing, in a medium appropriate for dyeing, from 0.01 to 4% by weight, relative to the total weight of the component (A), of at least 4-hydroxyindole or a salt thereof as a coupler and at least one oxidation dye precursor, the oxidation dye precursor and the coupler being present in proportions from 0.05 to 7% by weight, relative to the total weight of component (A), of an oxidation dye precursor, and a component (B) consisting of a composition containing an oxidizing agent in a sufficient amount to oxidize the coupler and oxidation dye precursor contained in component (A) and an acid component in a medium appropriate for dyeing, the acid component being present in a sufficient amount in component (B) such that, after mixing in proportions of 90 to 10% in respect of component (A) and of 10 to 90% in respect of component (B), the resulting composition has a pH of less than 7, said resulting composition being substantially free from an amount of iodide ions sufficient to oxidize 4-hydroxyindole and the oxidation dye precursor.

20. An agent according to claim 19, wherein
the component (A) has a pH of between 3 and 10.5.

21. An agent according to claim 19, in which component (A) contains a surface-active agent in a proportion of from 0.1 to 55% by weight, water, a solvent in addition to water in a proportion of between 0.5 and 40% by weight, a thickener in a proportion of between 0.1 and 5% by weight, an antioxidant in a proportion of between 0.02 and 1.5% by weight and any other cosmetically acceptable adjuvant.

22. An agent according to claim 19, in which the component (B) has a pH which has a minimum value of 1 and less than 7.

23. A method for dyeing keratinous fibre which comprises a first step consisting of storing separately the components (A) and (B) as defined in claim 19
and, before application, mixing the components (A) and (B) in proportions of 10 to 90% in respect of component (A) and of 90 to 10% in respect of component (B), so as to obtain a composition having a pH of less than 7, and applying this mixture immediately after preparation to the keratinous fibre.

24. A multi-compartment device or dyeing kit, which comprises at least two compartments, a first compartment of which contains the component (A) as defined in claim 19 and the second compartment contains the component (B) as defined in claim 19.

25. A device according to claim 24, which is fitted with means for permitting the desired mixture of components (A) and (B) to be delivered onto the keratinous fibre.

26. The agent of claim 19, wherein the acid component is an inorganic acid or an organic acid.

27. The agent of claim 26, wherein the inorganic acid is hydrochloric acid or phosphoric acid.

28. The agent of claim 26, wherein the organic acid is a carboxylic acid.

29. The agent of claim 28, wherein the carboxylic acid is tartaric acid or citric acid.

* * * * *